United States Patent [19]

Tsuchiya

[11] Patent Number: 4,461,572

[45] Date of Patent: Jul. 24, 1984

[54] INSTRUMENT FOR MEASURING LIGHT EMISSION INDUCED BY REPETITIVE STIMULATION OF THE SAME TYPE

[75] Inventor: Yutaka Tsuchiya, Hamamatsu, Japan

[73] Assignee: Hamamatsu TV Co., Ltd., Hamamatsu, Japan

[21] Appl. No.: 351,620

[22] Filed: Feb. 24, 1982

[30] Foreign Application Priority Data

Sep. 4, 1981 [JP] Japan ............................... 56-139584

[51] Int. Cl.³ .......................................... G01N 21/64
[52] U.S. Cl. .................... 356/318; 250/461.1
[58] Field of Search ....................... 356/317, 318, 417; 250/458.1, 459.1, 461.1, 213 VT

[56] References Cited

U.S. PATENT DOCUMENTS 4,403,140 9/1983 Tsuchiya ..................... 250/213 VT

FOREIGN PATENT DOCUMENTS 151222 10/1981 German Democratic Rep. ................................... 356/318

OTHER PUBLICATIONS

Stavolo et al., *Optical Communications*, vol. 34, No. 3, Sep. 1980, pp. 404–408.

Primary Examiner—F. L. Evans
Attorney, Agent, or Firm—Spencer & Frank

[57] ABSTRACT

Light emission to be observed is repeatedly started by starting means when each timing interval is maintained much longer than the sustaining time of the light emission. An image initiated by the starting means is incident on the photoelectric plate of an electron beam shutter tube when produced by imaging means. Sampling interval specifying means specifies different sampling interval for each occurrence of light emission if it detects the start of the starting means. Sutter tube driving means cuts the shuttering electric field during the sampling interval. Brightness on the phosphor screen due to an electronic image emitted during the sampling interval is converted into the corresponding electric signal by a photoelectric converter opposed to the phosphor screen of the shutter tube. The output signal of the photoelectric converter is stored in a memory device through a transferring means, and the contents of the memory device are displayed on displaying means or outputtted by an output device.

11 Claims, 7 Drawing Figures

INSTRUMENT FOR MEASURING LIGHT EMISSION INDUCED BY REPETITIVE STIMULATION OF THE SAME TYPE

BACKGROUND OF THE INVENTION

This invention relates to an instrument for measuring light emission, and particularly to an instrument for repeatedly measuring periodic light emission with high timing resolution when the light intensity, beam shape and spectral distribution fluctuate at ultrahigh speed.

When an organic molecular crystal is stimulated by light pulses, fluorescence with a lifetime of the order of $10^{-6}$ to $10^{-9}$ second occurs in this crystal. The characteristics of the crystal may be known determined by accurately measuring a profile of light intensity changes with time, and also by measuring the spectral distribution. If gas discharging and other fluctuating light emission may be measured with high precision, the performance of light emitting devices, the chemical and physical characteristics of materials, and their changes can be known.

An example of the conventional method for measuring light emission fluctuating at a high speed is described hereinafter with reference to a method for measuring the lifetime of fluorescence which may occur in an organic molecular crystal.

In the so-called sampling method, fluorescence occurs in a crystal to be observed when the crystal is stimulated by applying repetitive light pulses clocking at a rate ranging from several Hz to several MHz. The fluorescence induced by said stimulation is detected in a photomultiplier tube. The sampling pulse voltage generated in accordance with said stimulation is applied to the dinode of said photomultiplier tube or a mesh electrode (hereinafter referred to as a gate) across the electron beam path, and the sampling is carried out each time the crystal is stimulated. By totalling the results of the sampling operations, a fluorescent light intensity profile may be obtained corresponding the wavelengths of fluorescence.

In the so-called streaking camera method, a crystal is stimulated by emitting a single light pulse. The light of fluorescence induced by said stimulation is incident on the photoelectric layer of a streaking tube. When a deflection voltage synchronized with the stimulation light pulse is applied to the deflection plate of the streaking tube, an image characterized by an intensity proportional to the intensity of the light of fluorescence and also by a timing axis scanned by the deflection is displayed on the phosphor screen of the streaking tube. By analyzing the image, a fluorescent light intensity profile can be obtained.

In a third measuring method, a fluorescent light intensity profile is statistically obtained. According to the method, a crystal to be observed is stimulated by repetitive light pulses clocking at a rate ranging from several Hz to several MHz. The light intensity of fluorescence occurring in a crystal is decremented through a filter so as to obtain such a value that a single photon can be detected. The decremented fluorescent light intensity is detected in a photomultiplier tube. An integral circuit starts operation when the stimulation light pulse is emitted and it is stopped when an output pulse of the photomultiplier is emitted. (This type of integral circuit is called a time-to-voltage converter.) The number of cycles in a unit time is counted with time as a parameter by measuring time in terms of the integral circuit output voltage which can be measured with a multichannel crest voltmeter. The number of cycles in a unit time is plotted with the output voltage as a parameter, and a profile of the fluorescent light intensity proportional to the number of cycles counted with time which is represented in terms of the output voltage is thus obtained.

Said sampling method has been used often, but a photomultiplier tube can detect only a fluorescent light intensity change with time because it can detect only information related to light intensity. For the purpose of making an accurate sampling by this method, the photomultiplier tube must satisfactorily be operated during the sampling. Hence, the sampling pulse voltage must be kept unchanged during the sampling. However, it is not easy to generate a square wave voltage with an accurate narrow pulse width. This limits the timing resolution to $5 \times 10^{-9}$ second according to the sampling method.

In the above secondly mentioned streaking camera method, the timing resolution can be improved by increasing the voltage sweeping rate by rapidly changing the deflection voltage of the streaking tube. However, if the deflection voltage rate is increased so as to improve the timing resolution, sweeping on the phosphor screen is accomplished in a short period of time and it reduces the required measuring time. In other words, according to the streaking camera method an improvement in the timing resolution and increase of the measuring time do not conform, and they are not satisfied at the same time.

In the third and statistical method, the measurement is carried out by detecting a single photon and a number of sampling operations are required for a complete measurement. A relatively long period of time is thus required for measurement. For instance, if the sampling is carried out at 30 Hz, nine hours are required to accomplish the sampling of $10^6$ times during the measurement.

SUMMARY OF THE INVENTION

The instrument for measuring light emission, in accordance with the present invention, is effectively applicable to the measurement of light emission if stimulation to induce light emission which is essentially of the same type occurs repeatedly and the measuring instrument according to the present invention consists of the following basic components.

An electron beam shutter tube comprising a photoelectric layer, channeling plates providing a number of electron beam paths, a phosphor screen, and a shuttering electrode to generate a shuttering electric field perpendicular to said electron beam paths is used to convert a light pulse into a corresponding electric signal and also for sampling.

Light emission to be observed is repeatedly started by starting means when each timing interval is maintained much longer than the light emission sustaining time. An image initiated by said starting means is incident on the photoelectric plate of said electron beam shutter tube when produced by the imaging means. Sampling interval specifying means specifies a different sampling interval for each occurrence of light emission if it detects the start of said starting means. Shutter tube driving means cuts the shuttering electric field during said sampling interval. Brightness on the phosphor screen due to an electronic image taken out during said sampling interval is converted into the corresponding electric signal by the photoelectric converter opposed to the phosphor screen of said shutter tube. The output signal of said photoelectric converter is stored in a memory device through the transferring means.

The contents of the memory device are displayed on displaying means or outputted by an output device.

A combination of the phosphor screen of the electron beam shutter tube mentioned above and the photoelectric converter opposed to the phosphor screen can be replaced with a solid-state image sensor which can convert an electron image into the corresponding picture signal.

DESCRIPTION OF THE PREFERRED EMBODIMENTS

Figure 1:
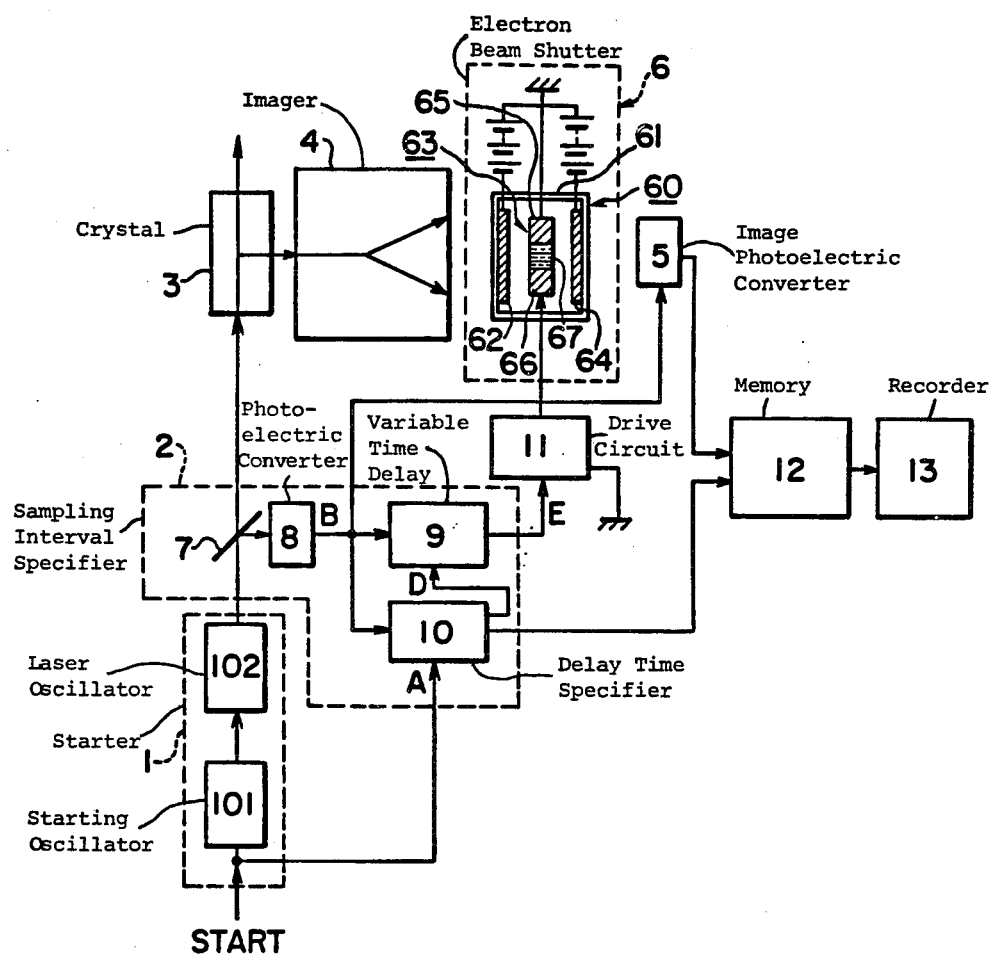
FIG. 1 is a block diagram showing a first embodiment of the instrument for measuring light emission in accordance with the present invention.
Figure 2:
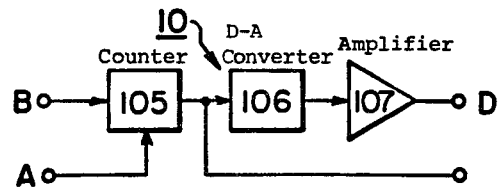
FIG. 2 is a block diagram showing an example of the delaying time specifying means included in the sampling interval specifying means 2.
Figure 5:
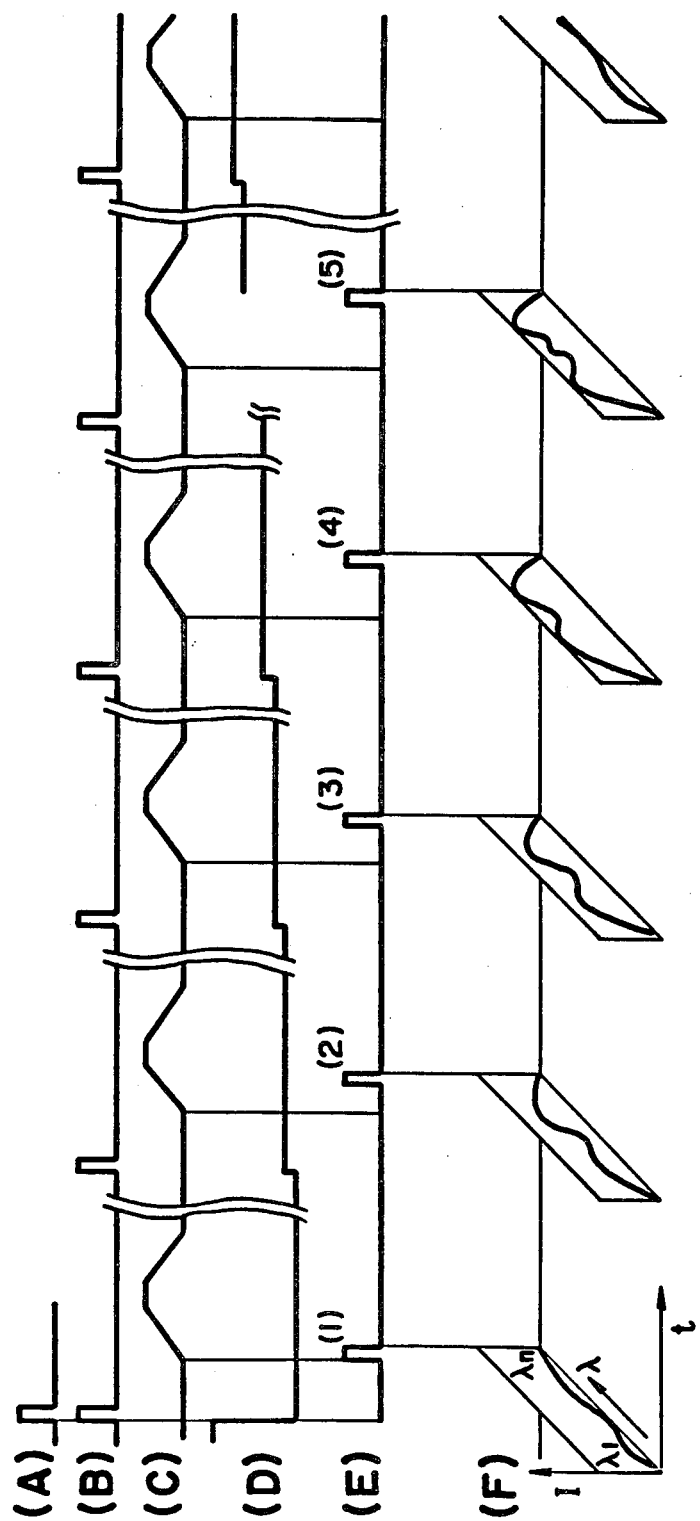
FIG. 5 shows a series of plots used to explain the operation of the measuring instrument shown in FIG. 1.

FIG. 1 is a block diagram of an instrument for measuring a spectral distribution change with time for an organic molecular crystal by the first embodiment of the instrument for measuring light emission. FIG. 5 shows a waveform diagram illustrating the operation of said measuring instrument of FIG. 1. Starting means 1 consists of a starting oscillator 101 and a laser oscillator 102 which emits light pulses at an interval given by the starting clock signal sent from the oscillator 101. The oscillator 101 starts its operation when a starting instruction (see FIG. 5, (A)) is issued and thereafter stimulates the laser oscillator 102 at given timing intervals. In this embodiment, a mode synchronizing YAG laser and a laser oscillator consisting of a fourth harmonic generator are used as the laser oscillator 102. The laser device 102 starts oscillation each time it receives the starting clock pulse signal from the oscillator 101 and emits a UV laser beam with a pulse width of 30 ps at a wavelength of 266 nm (see FIG. 5, (B)). The UV laser beam is partly split by an optical splitter 7 installed in the starting means 1 and the other part of the UV laser beam is incident on an organic molecular crystal acting as the light emission source 3 to be observed. The organic molecular crystal 3 is stimulated by the laser beam and emits fluorescent light as shown in FIG. 5, (C). The delay time from the stimulation to the fluorescent light emission, the spectral distribution of the fluorescent light, and the lifetime at each wavelength depend on the type of crystal and the impurity concentration as well as the state of the crystal and their analysis is thus important. When crystaline anthracene is stimulated by the UV ray, it is well known that the delay time from the stimulation to the light emission is on the order of $10^{-10}$ to $10^{-7}$ sec, and that the lifetime of fluorescence for crystaline anthracene is on the order of $10^{-9}$ sec. or above. Fluorescent light from an organic molecular crystal to be observed is dispersed depending on the wavelengths from a spectroscope identified as imaging means 4 and is then incident on the photoelectric layer 62 of an electron beam shutter tube 60 in an electron beam shutter 6. Locations through which the fluorescent light is incident on the photoelectric layer 62 are determined corresponding to the wavelengths. Electrons are emitted from the respective locations on the photoelectric layer, corresponding to the fluorescent light intensity obtained at the respective wavelengths. The UV ray branching at the optical splitter 7 made of a semi-transparent mirror is partly incident on a photoelectric converter 8 of a sampling interval specifying means 2 for the stimulation of light pulses. The photoelectric converter 8 consisting of a PIN photodiode issues generates an electric signal responding to the UV ray incident on the photodiode at a response time of up to 1 ns. In this case, the primary ray of the mode synchronizing YAG laser may be incident on the PIN photodiode. The output terminal of the photoelectric converter 8 is connected to an imaging photoelectric converter 5 consisting of a linear photosensor, a variable time delay circuit 9, and a delaying time specifying circuit 10. The delay time specifying circuit 10 counts output pulses of the photoelectric converter 8 (see FIG. 3, B), and an output voltage is generated corresponding to the number of counted pulses, which is shown in FIG. 5, (D). An example of the configuration of the delay time specifying circuit 10 will be described with reference to FIG. 2. The delay time specifying circuit 10 comprises a counter 105, a digital-to-analog converter 106 and an analog amplifier 107. The counter 105 is reset by the starting signal (see FIG. 5, (A)) of a starting block 1 when the measurement starts. After the resetting the counter 105 starts counting output pulses (see FIG. 5, (B)) of the photoelectric converter 8. The digital-to-analog converter 106 converts the number of pulses counted by the counter 105 in a unit time into the corresponding voltage, and the analog amplifier 107 amplifies the voltage to a level such that the variable time delay circuit 9 can be driven. An explanation of the variable time delay circuit 9 follows.

The variable time delay circuit 9 delays the output pulses (see FIG. 5, (B)) of said photoelectric converter 8 for converting light pulses generated by optical stimulus. The delay time is determined by the output voltage (see FIG. 5, (D)) of the delay time specifying circuit 10.

Figure 3:
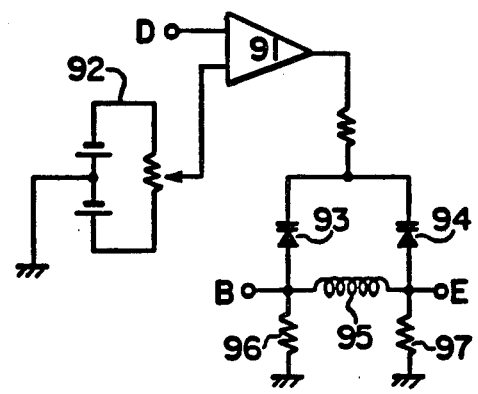
FIG. 3 is a circuit diagram showing an example of the variable time delaying circuit included in the sampling interval specifying means.

An example of the configuration of the variable time delay circuit 9 will be described with reference to FIG. 3. A variable voltage source 92 supplies a positive or negative voltage selected by a switch. An operational amplifier 91 of the variable delay circuit 9 adds the output voltage (see FIG. 5, (D)) of said delay time specifying circuit 10 and the output voltage of the variable voltage source 92. The cathode terminals of variable capacitance diodes 93 and 94, which are tied together, are connected to the output terminal of the operational amplifier 91 through a resistor. Assuming that the capacitances of the variable capacitance diodes 93 and 94 are 'C' and that the inductance of a coil 95 is 'L', a voltage delayed by $\sqrt{2LC}$ from the voltage at the nodal point of the variable capacitance diode 93 and resistor 96 appears at the nodal point of the variable capacitance diode 94 and resistor 97. When the voltage across the terminals of each variable capacitance diode is changed from 5 volts to 30 volts, the diode capacitance varies from 15 pF to 5 pF. If the coil 95 has an inductance of 100 μH, the maximum delay time change due to said voltage change is 0.5 ns. The capacitances of the variable capacitance diodes 93 and 94 vary in accordance with the voltages across their terminals, respectively. If the output voltage of the variable voltage source 92 is kept constant, said delay time can be changed by a voltage applied to the other input terminal of the operational amplifier 91 or in other words by the output voltage (see FIG. 5, (D)) of the delay time specifying circuit 10. Hence, the delay time increases as the mode synchronizing YAG laser 102 increases light emission. FIG. 5, (E) shows a delayed pulse train. The output terminal of the variable time delay circuit 9 is connected with the input terminal of a shutter tube driving circuit 11. In addition, an emitter coupled monostable multivibrator is used as means for generating a longer variable delay time. In this case, the time of the quasi-stable state is controlled by the output voltage of the delay time specifying circuit 10. For instance, it can be actualized by applying the output voltage of the delay time specifying circuit 10 to the base of the emitter coupled monostable multivibrator.

Figure 4:
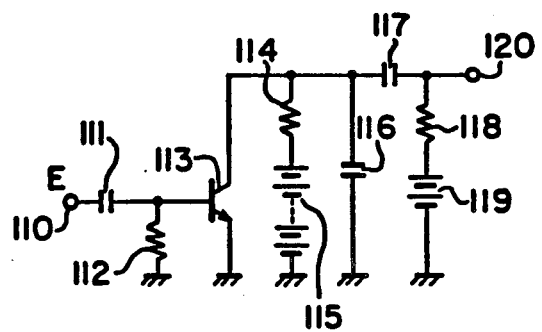
FIG. 4 is a circuit diagram showing an example of the shutter tube driving circuit.

An example of the configuration of the shutter tube driving circuit 11 will be described with reference to FIG. 4. The circuit 11 can generate a ramp voltage which goes to −100 V starting from +100 V at a rate of 1 KV/ns. A lead of a resistor 114 is connected to the positive output terminal of a 200-volt constant voltage source 115, while a lead of a resistor 118 is connected to the positive output terminal of a 100-voltage constant voltage source 119. The other leads of the respective resistors 114 and 118 are connected to a capacitor 117. The negative terminals of these constant voltage sources are connected to ground. The emitter of an avalanche transistor 113 is connected to ground, and its collector is connected to the nodal point of said resistor 114 and capacitor 117. A capacitor 116 is connected in parallel with a series circuit composed of the voltage source 115 and the resistor 114. The potential at the output terminal 120 of the capacitor 117 is kept at 100 volts by the voltage source 119, while the potential at the nodal point of the avalanche transistor 113 and capacitor 117 is kept at 200 volts by the voltage source 115.

When the pulse voltage (see FIG. 5, (E)) from the variable time delay circuit 9 is applied to the input terminal 110, the avalanche transistor 113 conducts and the voltage at the nodal point of the avalanche transistor 113 and capacitor 117 abruptly goes to 0 volt starting at 200 volts. The potential at the output terminal 120 of the shutter tube driving circuit 11 then goes to −100 volts starting at +100 volts. The avalanche transistor 113 can quickly respond to such an abrupt voltage change, and thus the output voltage can vary at a rate of 1 KV/ns. This abrupt voltage change plays the role of shuttering the electron beam in the electron beam shuttering device 6.

This voltage change is applied to the terminals across the shutter 63 of the electron beam shutter tube 60.

The electron beam shutter tube 60 consists of a cylindrical envelope with a diameter of one inch (25.4 mm), on the inner surface of which a photoelectric layer 62 of a cesium-antimony compound is partly formed. The photoelectric layer 62 is kept at −1 KV. Another layer facing said photoelectric layer 62 is a phosphor screen 64. A shutter 63 is provided between said photoelectric layer 62 and the phosphor screen 64.

The electron beam shutter described herein is related to a patent application (Japanese patent application No. 116241/1980) of the applicant of this invention and it is described in detail in its specification. The invention of the preceding application is summarized as follows: The shutter plate 63 consists of a pair of upper and lower electrodes 65 and 66. A channel plate 67 having an appropriate resistance value is provided between the pair of electrodes 65 and 66. A number of holes are bored in this plate 67 in the direction perpendicular to the electric field formed by said electrodes 65 and 66, or in parallel with the axis of the tube. When the voltage across said electrodes 65 and 66 is set at 0 volt, said holes form electronic paths and electrons can pass therethrough from one side to the other. If an electric field is generated in the gap between the pair of said electrodes, electrons within these holes are trapped by said plate 67 so as to close the shutter. The shutter tube 60 can act as a shutter for two-dimensionally distributed electrons forming an image. The holes of the shutter 63 in the electron beam shutter tube 60 used in the measuring instrument of the present application have inner diameters of 200 microns and are 4 mm in length. The plate 67 with holes forms a stripe with a width of 1 mm and has a pair of electrodes at both sides. The span between the shutter 63 and the photoelectric plate 62 measures 2 mm. The phosphor screen 64 is kept at +3 KV. The axis of holes bored in the shutter 63 of the electron beam shutter tube 60 is in parallel with the electric field to accelerate photoelectrons in a space between the photoelectric layer 62 and the phosphor screen 64. Photoelectrons are accelerated by one kilovolts and are perpendicularly incident on the shutter 63. If the above mentioned voltage which changes at a rate of 1 KV/ns is applied to the shutter 63, photoelectrons can pass through the holes for a time of 50 picoseconds before it goes to 0 volt. If fluorescence with a lifetime of 1 ns occurs in the organic molecular crystal 3, photoelectrons can pass for a finite period of time which is equal to one twentieth of 1 ns. This means that as many electrons as those corresponding to the intensity of light induced by fluorescence at each wavelength can pass through the shutter 63 and hit the phosphor screen. And corresponding to the fluorescent light intensity, the spectral line distribution spreads forth in the direction of the width of the phosphor screen. FIG. 5, (F) shows plots of the intensity I on the vertical axis, represented in terms of wavelength on the horizontal axis as a parameter.

If the variable time delay circuit 9 is adjusted by appropriately setting the output voltage of the delay time specifying circuit 10 so as to increment the delay time by 50 picoseconds each time a pulse voltage is generated by the PIN photodiode 8, bright spots are displayed on the phosphor screen 64 as shown in FIG. 5, (F) corresponding to the fluorescent light intensity over the entire band of wavelengths.

The longitudinal direction of brightness distribution on the phosphor screen 64 is called hereinafter the coordinate wavelengths. The direction of λ in FIG. 5, (F) indicates the coordinate of wavelengths. The coordinate of wavelengths conforms the direction of wavelength dispersion occurring in the spectroscope 4 and it is perpendicular to the axis of the holes in the shutter 63.

A photoelectric converter 5 is provided facing the phosphor screen 64. In this embodiment a one-dimensional linear photosensor consisting of 256 picture elements arranged in the coordinate of wavelengths so as to conform the coordinate of wavelengths with the axis of scanning is located facing the phosphor screen 64. The photoelectric converter 5 consisting of a linear photosensor operates synchronously with the output pulse voltage of the photoelectric converter 8 having a PIN photodiode for receiving the stimulation light pulses. The linear photosensor provides 256 picture elements, each of which responds to the light intensity at a given wavelength. Before the next sampling, information stored in each picture element is transferred to a memory device 12 having areas at least equal to the number of picture elements on the coordinate of wavelengths multiplied by the number of times of sampling.

In the preferred embodiment described herein, the number of times of sampling is 20 and a memory device having at least 256×20 areas for storing must be used.

A plot of the spectral intensity response is displayed on the phosphor screen 64 of the electron beam shutter tube 60 each time 50 picoseconds elapses after the photoelectric converter 8 consisting of a PIN photodiode emits a pulse signal. The light intensity signal of the spectral response is thus converted into the corresponding electric signal by a linear photosensor consisting of 256 picture elements each time the phosphor screen emits a light signal and it is then transferred to the memory device 12 where information is stored in all 256×20 locations by 20 successive sampling operations. This is a complete cycle of the measurement. An example of the processing of the memory contents will now be described. If the memory contents at specific wavelengths are repeatedly read and displayed on an X-Y recorder 13, a profile of the light intensity change represented in terms of wavelengths can be obtained. If an optical lens is used as imaging means 4 in place of a spectroscope, a two-dimensional image to be observed is formed on the photoelectric layer 62.

In such a case, the shutter can cut photoelectrons having a distribution in two dimensions. An imaging device such as a two-dimensional solid-state imaging device or a Vidicon tube forms the photoelectric converter 5.

Figure 6:
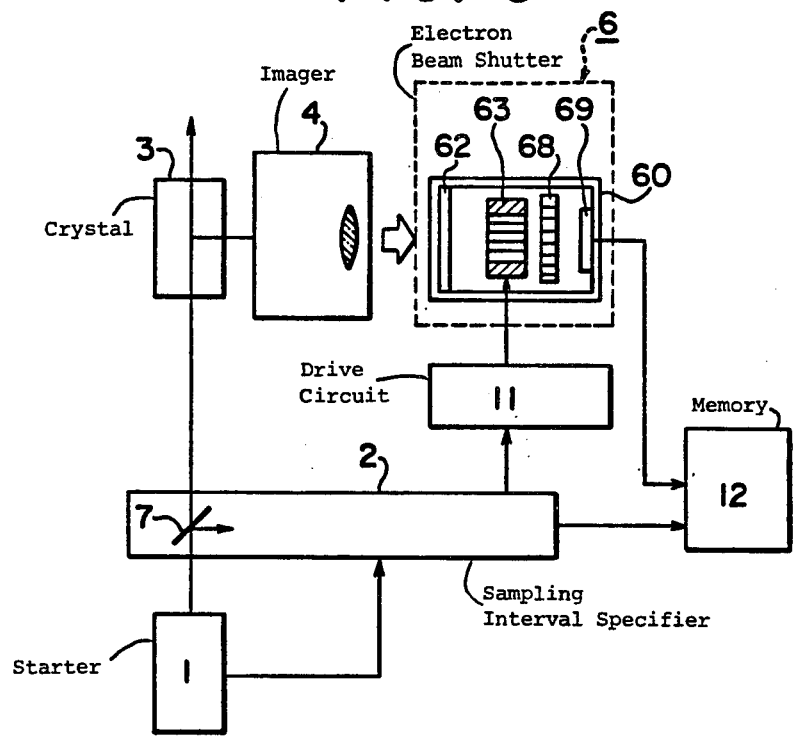
FIG. 6 is a diagram showing a second embodiment of the measuring instrument of the present invention.

FIG. 6 is a block diagram showing another preferred embodiment of the instrument for measuring light emission in accordance with the present invention. A self-scanned solid-state imaging photodiode array has been widely used as a visible light sensing device. This device can be used as an electron sensor as well as said visible light sensor. In the electron beam shutter tube 60 used in this second embodiment, a solid-state imaging device 69 is installed in a location where the phosphor screen of the shutter tube 60 described above is to be set and it can thus act as the phosphor screen 64, such as used in the first embodiment, as well as the photoelectric converter 5. Other elements of this second embodiment are the same as those in the first embodiment. A channeling plate 68 is installed in the electron beam shutter tube 60 so as to multiply photoelectrons having passed through the shutter 63 under the control of the sampling. The channeling plate can also be installed in the electron beam shutter tube of the first embodiment in the same manner as in this embodiment.

Figure 7:
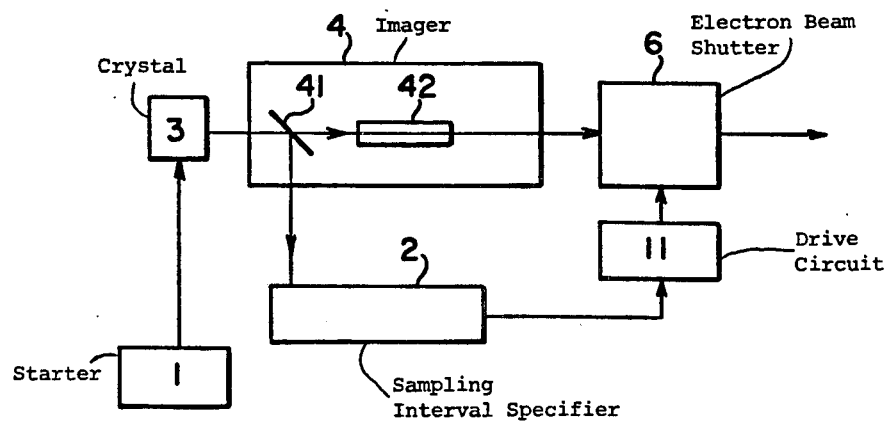
FIG. 7 is a block diagram depicting a variation of the imaging means.

If timing spans between stimulation of an organic molecular crystal by laser beam and emission of light by fluorescence fluctuate, the reference timing cannot be determined in some cases by detecting the laser beam as described in the first embodiment. FIG. 7 is a block diagram showing a variation which is suitable for such a case as mentioned above. In such a variation, an optical splitting device 41 is attached to or located before the imaging means 4 and then the fluorescent light is partly transmitted to the sampling interval specifying means 2. In the sampling interval specifying means 2, a PIN photodiode detects light pulses in the same manner as in the first embodiment, and a signal specifying the sampling interval is thus generated. On the other hand, in the imaging means 4, an image is formed on the photoelectric layer 62 of the electron beam shutter tube 60 by delaying the fluorescent light which passed through said optical splitting device 41 with optical delay means 42. This eliminates the effects of the fluctuation phenomena on the sampling accuracy.

The instrument for measuring light emission of the present invention provides the configuration described above and it can thus measure light emission with a timing resolution higher than any of the conventional methods.

Light emission can occur at arbitrary timing intervals, and occurrence of light emission can be controlled at appropriate timing intervals by taking the lifetime of light emission into account. The timing resolution is not necessarily always lowered for such a reason as described above. Sampling of the electron beam obtained by a two-dimensional image formed with a lens system, as well as sampling of a one-dimensional image such as in the spectral distribution, can be done by the electron beam shutter tube. This enables one to measure optical images that could not have been measured before.

As for the preferred embodiments herein described in detail, a number of variations are possible within the scope of the invention. For example, the reflected or transmitted light which may change abruptly must be recognized as light emission as defined in the present invention.

What is claimed is:

1. An instrument for measuring light emission induced by repetitive stimulation of the same type comprising:

an electron beam shutter tube including a photoelectric layer, channel plates having a plurality of electron beam paths, a phosphor screen and a shutter electrode for generating a shuttering electric field perpendicular to said electron beam paths;

starting means for successively starting said light emission at timing intervals much longer than the sustaining time of said light emission;

imaging means for forming an image of said light emission initiated by said starting means on the photoelectric layer of said electron beam shutter tube;

sampling interval specifying means for generating signals specifying different sampling intervals for different types of light emission upon detecting the start of said light emission;

a shutter tube driving device for driving said shutter tube so as to cut the shuttering electric field at said sampling intervals;

a photoelectric converter located facing the phosphor screen of said shutter tube, said photoelectric converter converting bright spots on said phosphor screen into corresponding electric signals at said sampling intervals;

transferring means for transferring the output of said photoelectric converter before the next sampling operation starts; and means for storing or displaying the output of said transferring means.

2. An instrument for measuring light emission as defined in claim 1, wherein the starting means for initiating said light emission is a light source generating light pulses at given intervals, said light emission being induced by stimulation of materials with said light pulses.

3. An instrument for measuring light emission as defined in claim 2, wherein said materials are organic molecular crystals.

4. An instrument for measuring light emission as defined in claim 2, wherein said light source is a laser device.

5. An instrument for measuring light emission as defined in claim 1, wherein said imaging means includes a spectroscope which disperses light emitted from the light source to be observed in accordance with the wavelengths thereby; the optical energy of the dispersed light at each wavelength being incident on the photoelectric layer of said electron beam shutter tube and the dispersed light travelling in the direction perpendicular to said shuttering electric field.

6. An instrument for measuring light emission as defined in claim 1, wherein said imaging means is a lens system which receives, as a two-dimensional image, light emission of the light source to be observed and then forms a two-dimensional image on the photoelectric layer of said electron beam shutter tube.

7. An instrument for measuring light emission as defined in claim 1, wherein said imaging means includes a slit, the photoelectric layer only sensing light having passed through said slit, and said photoelectric converter is a photomultiplier tube, said slit being located perpendicular to said shuttering electric field.

8. An instrument for measuring light emission as defined in claim 1, wherein said photoelectric converter is a solid-state imaging device.

9. An instrument for measuring light emission as defined in claim 4, wherein the start of said sampling interval specifying means is detected by sensing light pulses emitted from said laser device.

10. An instrument for measuring light emission as defined in claim 1, wherein the start of signals from said sampling interval specifying means is detected by sensing light emission induced by said stimulation, said imaging means optically delaying light emission induced by said stimulation so as to conduct the light beam to the photoelectric layer of said electron beam shutter.

11. An instrument for measuring light emission induced by repetitive stimulation of the same type comprising:

an electron beam shutter tube including a photoelectric layer, channel plates having a plurality of electron beam paths, an imaging target for storing imaging currents in its respective locations, and a shutter electrode for generating a shuttering electric field perpendicular to said electron beam paths;

starting means for successively starting said light emission at timing intervals much longer than the sustaining time of said light emission;

imaging means for forming an image of said light emission initiated by said starting means on the photoelectric layer of said electron beam shutter tube;

sampling interval specifying means for generating signals specifying different sampling intervals for different types of light emission upon detecting the start of said light emission;

a shutter tube driving device for driving said shutter tube so as to cut the shuttering electric field at said sampling intervals;

transferring means for transferring the output of each element in said imaging target before the next sampling operating starts; and means for storing the output of said transferring means.

* * * * *